(12) United States Patent
Hunt et al.

(10) Patent No.: US 9,345,586 B2
(45) Date of Patent: May 24, 2016

(54) VARIABLE ANGLE SPINAL SURGERY INSTRUMENT

(75) Inventors: Margaret M. Hunt, Cedar Park, TX (US); Anthony P. Moreno, Tampa, FL (US); Scott A. Webb, Largo, FL (US)

(73) Assignee: Zimmer Spine, Inc., Edina, MN (US)

( * ) Notice: Subject to any disclaimer, the term of this patent is extended or adjusted under 35 U.S.C. 154(b) by 1330 days.

(21) Appl. No.: 12/698,691

(22) Filed: Feb. 2, 2010

(65) Prior Publication Data

US 2010/0137922 A1    Jun. 3, 2010

Related U.S. Application Data

(63) Continuation of application No. 11/257,745, filed on Oct. 25, 2005, now abandoned, which is a continuation-in-part of application No. 10/633,371, filed on Aug. 1, 2003, now Pat. No. 7,806,932.

(60) Provisional application No. 60/623,274, filed on Oct. 29, 2004.

(51) Int. Cl.
*A61B 17/70* (2006.01)
*A61F 2/46* (2006.01)
(Continued)

(52) U.S. Cl.
CPC ............ *A61F 2/4611* (2013.01); *A61B 17/1671* (2013.01); *A61B 17/1659* (2013.01);
(Continued)

(58) Field of Classification Search
CPC ........... A61F 2002/4628; A61F 2/4611; A61F 2/4603; A61F 2002/4623; A61F 2002/4627; A61B 17/1757

USPC .......... 623/17.11–17.16; 606/90, 91, 99, 100, 606/86 A, 86 R, 914
See application file for complete search history.

(56) References Cited

U.S. PATENT DOCUMENTS 3,867,728 A    2/1975  Stubstad et al.
4,743,256 A    5/1988  Brantigan
(Continued)

FOREIGN PATENT DOCUMENTS

DE    29901611    6/1999
DE    19903762 C1    11/2000
(Continued)

OTHER PUBLICATIONS

Partial International Search Report for PCT Application No. PCT/US2004/023721, issued on Jul. 12, 2004, 8 pgs.
(Continued)

*Primary Examiner* — Matthew Lawson
(74) *Attorney, Agent, or Firm* — Schwegman Lundberg & Woessner, PA..

(57) ABSTRACT

An instrument for use in a procedure for inserting a spinal implant between human vertebrae may include a shaft and an end member. The end member may rotate with respect to the shaft. An angle of the end member with respect to the shaft may be varied when the end member is in a disc space between the human vertebrae. The instrument may include a slide for securing the end member at selected angles relative to the shaft. The end member may be separable from the shaft when the end member is in a selected orientation with the shaft. An instrument kit may include a shaft assembly and modular end members for various steps in a surgical procedure, such as disc space preparation, disc space evaluation, and spinal implant insertion.

21 Claims, 10 Drawing Sheets

(51) Int. Cl.
*A61B 17/16* (2006.01)
*A61B 17/00* (2006.01)
*A61F 2/44* (2006.01)
*A61F 2/30* (2006.01)

(52) U.S. Cl.
CPC ............... *A61B2017/00464* (2013.01); *A61B 2017/00469* (2013.01); *A61F 2/4465* (2013.01); *A61F 2002/30133* (2013.01); *A61F 2002/30523* (2013.01); *A61F 2002/30538* (2013.01); *A61F 2002/4627* (2013.01); *A61F 2002/4628* (2013.01); *A61F 2220/0025* (2013.01); *A61F 2230/0015* (2013.01); *A61F 2250/0006* (2013.01)

(56) References Cited

U.S. PATENT DOCUMENTS

| | | | |
|---|---|---|---|
| 4,768,787 A | 9/1988 | Shira | |
| 4,834,757 A | 5/1989 | Brantigan | |
| 4,878,915 A | 11/1989 | Brantigan | |
| 4,964,641 A | 10/1990 | Miesch et al. | |
| 5,019,081 A | 5/1991 | Watanabe | |
| 5,171,278 A | 12/1992 | Pisharodi | |
| 5,192,327 A | 3/1993 | Brantigan | |
| 5,306,307 A | 4/1994 | Senter et al. | |
| 5,425,772 A | 6/1995 | Brantigan | |
| 5,429,863 A | 7/1995 | McMillin | |
| 5,443,514 A | 8/1995 | Steffee | |
| 5,526,664 A | 6/1996 | Vetter | |
| 5,609,635 A | 3/1997 | Michelson | |
| 5,653,763 A | 8/1997 | Errico et al. | |
| 5,713,899 A | 2/1998 | Marnay | |
| 5,716,415 A | 2/1998 | Steffee | |
| 5,717,006 A | 2/1998 | Daculsi et al. | |
| 5,733,290 A | 3/1998 | McCue et al. | |
| 5,766,252 A | 6/1998 | Henry et al. | |
| 5,769,897 A | 6/1998 | Harle | |
| 5,814,084 A | 9/1998 | Grivas et al. | |
| 5,836,958 A | 11/1998 | Ralph | |
| 5,888,227 A | 3/1999 | Cottle | |
| 5,918,821 A | 7/1999 | Grooms et al. | |
| 5,984,922 A | 11/1999 | McKay | |
| 5,989,289 A | 11/1999 | Coates et al. | |
| 6,025,538 A | 2/2000 | Yaccarino, III | |
| 6,113,639 A | 9/2000 | Ray et al. | |
| 6,143,032 A | 11/2000 | Schafer et al. | |
| 6,143,033 A | 11/2000 | Paul et al. | |
| 6,159,211 A | 12/2000 | Boriani et al. | |
| 6,174,311 B1 | 1/2001 | Branch et al. | |
| 6,190,414 B1 * | 2/2001 | Young et al. ............... | 623/17.15 |
| 6,200,347 B1 | 3/2001 | Anderson et al. | |
| 6,224,607 B1 | 5/2001 | Michelson | |
| 6,241,770 B1 | 6/2001 | Michelson | |
| 6,245,108 B1 | 6/2001 | Biscup | |
| 6,277,149 B1 | 8/2001 | Boyle et al. | |
| 6,290,724 B1 | 9/2001 | Marino | |
| 6,294,187 B1 | 9/2001 | Boyce et al. | |
| 6,346,123 B1 | 2/2002 | McKay | |
| 6,468,311 B2 | 10/2002 | Boyd et al. | |
| 6,517,544 B1 | 2/2003 | Michelson | |
| 6,530,956 B1 | 3/2003 | Mansmann | |
| 6,537,589 B1 | 3/2003 | Chae et al. | |
| 6,579,318 B2 | 6/2003 | Varga et al. | |
| 6,599,294 B2 | 7/2003 | Fuss et al. | |
| 6,613,089 B1 | 9/2003 | Estes et al. | |
| 6,648,915 B2 | 11/2003 | Sazy | |
| 6,682,534 B2 | 1/2004 | Patel et al. | |
| 6,699,288 B2 | 3/2004 | Moret | |
| 6,719,794 B2 | 4/2004 | Gerber et al. | |
| 6,764,491 B2 | 7/2004 | Frey et al. | |
| 6,830,570 B1 | 12/2004 | Frey et al. | |
| 6,852,127 B2 | 2/2005 | Varga et al. | |
| 6,974,480 B2 | 12/2005 | Messerli et al. | |
| 7,060,073 B2 | 6/2006 | Frey et al. | |
| 7,500,991 B2 | 3/2009 | Bartish, Jr. et al. | |
| 7,806,932 B2 | 10/2010 | Webb et al. | |
| 2001/0021853 A1 | 9/2001 | Heckele et al. | |
| 2002/0077700 A1 | 6/2002 | Varga et al. | |
| 2002/0087212 A1 | 7/2002 | James et al. | |
| 2002/0143400 A1 | 10/2002 | Biscup | |
| 2002/0165612 A1 | 11/2002 | Gerber et al. | |
| 2002/0177897 A1 * | 11/2002 | Michelson ............... | 623/17.11 |
| 2003/0069586 A1 * | 4/2003 | Errico et al. ............... | 606/99 |
| 2003/0100950 A1 | 5/2003 | Moret | |
| 2003/0114931 A1 * | 6/2003 | Lee ............... | A61F 2/4611 623/17.11 |
| 2004/0127990 A1 | 7/2004 | Bartish, Jr. et al. | |
| 2004/0153065 A1 * | 8/2004 | Lim ............... | 606/53 |
| 2005/0004671 A1 | 1/2005 | Ross et al. | |
| 2005/0027360 A1 | 2/2005 | Webb et al. | |
| 2005/0096745 A1 * | 5/2005 | Andre et al. ............... | 623/17.11 |
| 2006/0004376 A1 * | 1/2006 | Shipp et al. ............... | 606/99 |
| 2006/0074427 A1 * | 4/2006 | Lieberman ............... | 606/84 |
| 2006/0095043 A1 * | 5/2006 | Martz et al. ............... | 606/90 |
| 2006/0229627 A1 | 10/2006 | Hunt et al. | |
| 2006/0241761 A1 | 10/2006 | Gately | |
| 2007/0142843 A1 | 6/2007 | Dye | |
| 2007/0213737 A1 * | 9/2007 | Schermerhorn et al. ........ | 606/86 |
| 2007/0213826 A1 * | 9/2007 | Smith et al. ............... | 623/17.11 |
| 2007/0225726 A1 | 9/2007 | Dye | |
| 2007/0225808 A1 | 9/2007 | Warnick | |
| 2008/0009880 A1 | 1/2008 | Warnick et al. | |
| 2008/0027544 A1 | 1/2008 | Melkent | |
| 2008/0065082 A1 | 3/2008 | Chang et al. | |
| 2008/0077150 A1 | 3/2008 | Nguyen | |
| 2008/0077241 A1 | 3/2008 | Nguyen | |
| 2008/0091211 A1 | 4/2008 | Gately | |
| 2008/0132901 A1 * | 6/2008 | Recoules-Arche et al. .... | 606/99 |
| 2010/0256760 A1 * | 10/2010 | Hansell ............... | 623/17.11 |

FOREIGN PATENT DOCUMENTS

| | | |
|---|---|---|
| FR | 2736537 | 1/1997 |
| JP | 09-122160 | 5/1997 |
| JP | 2002503135 T | 1/2002 |
| JP | 3692169 | 6/2005 |
| WO | WO9715248 A | 5/1997 |
| WO | WO 9817209 | 4/1998 |
| WO | WO 98/56319 A1 | 12/1998 |
| WO | WO 00/44288 | 8/2000 |
| WO | WO0128469 A2 | 4/2001 |
| WO | WO0154629 A1 | 8/2001 |
| WO | WO 02/17823 A1 | 3/2002 |
| WO | WO0247587 A2 | 6/2002 |

OTHER PUBLICATIONS

Examination Report issued for European Patent Application No. 04 778 983.9, mailed Jun. 10, 2011, 4 pgs.
International Search Report issued in U.S. Patent Application No. PCT/US2004/023721 mailed Apr. 11, 2005, 8 pgs.
International Preliminary Report on Patentability dated Feb. 6, 2006 in PCT/US2004/02372, 12 pgs.
Examination Report dated Jul. 3, 2009 in Australian Patent Application No. 2004261160, 3 pgs.
Captiva Spine Receives 510(k) Clearance for its Proprietary Lumbar Interbody Fusion Device, the Pivotec, Captiva Spine, Inc., Jupiter, FL, Dec. 9, 2009, at http://www.pr.com/press-release/197472, 2 pgs.
Office Action issued in U.S. Appl. No. 10/633,371 mailed Jun. 5, 2006, 6 pgs.
Office Action issued in U.S. Appl. No. 10/633,371 mailed Dec. 9, 2008, 8 pgs.
Office Action issued in U.S. Appl. No. 10/633,371 mailed Apr. 1, 2009, 8 pgs.
Office Action issued in U.S. Appl. No. 11/257,745 mailed Dec. 11, 2008, 7 pgs.
Office Action issued in U.S. Appl. No. 11/257,745 mailed Oct. 2, 2009, 7 pgs.
Examination Report dated Apr. 6, 2010 in Australian Patent Application No. 2004261160, 1 pg.

(56) References Cited

OTHER PUBLICATIONS

Office Action and its English Translation issued in Japanese Patent Application No. 2006-521937, issued May 26, 2010, mailed Jun. 1, 2010, 6 pgs.

Office Action issued in U.S. Appl. No. 12/854,760, mailed Dec. 27, 2011, 8 pages.

Office Action issued in U.S. Appl. No. 10/633,371, issued on Apr. 12, 2010, 9 pgs.

Office Action issued in Canadian Patent Application No. 2,534,357, mailed Feb. 11, 2010, 3 pgs.

Office Action issued in Japanese Patent Application No. 2006-521937, issued Jan. 14, 2010, mailed Jan. 19, 2010, 8 pgs.

\* cited by examiner

VARIABLE ANGLE SPINAL SURGERY INSTRUMENT

CROSS-REFERENCE TO RELATED APPLICATION

This application is a continuation of, and claims a benefit of priority under 35 U.S.C. 120 of the filing date of U.S. patent application Ser. No. 11/257,745 by inventors Margaret M. Hunt at al. entitled "Variable Angle Spinal Surgery Instrument" filed on Oct. 25, 2005, now abandoned which in turn claims the benefit of priority under 35 U.S.C. §119 to provisional patent application No. 60/623,274 filed Oct. 29, 2004; and is a continuation in part of, and claims a benefit of priority under 35 U.S.C. 120 of the filing date of U.S. patent application Ser. No. 10/633,371 by inventors Scott A. Webb et al. entitled "Spinal Implant" on Aug. 1, 2003, now U.S. Pat. No. 7,806,932 the entire contents of which are hereby expressly incorporated by reference for all purposes.

BACKGROUND

1. Field of Invention

The present invention generally relates to the field of medical devices, Some embodiments of the invention relate to instruments used during surgical procedures to install a spinal implant in a human spine. Some embodiments of the invention relate to instruments used in evaluating and/or preparing a disc space for a spinal implant. Some embodiments of the invention relate to an instrument used to manipulate and/or position a spinal implant between human vertebrae.

2. Description of Related Art

An intervertebral disc may degenerate. Degeneration may be caused by trauma, disease, and/or aging. An intervertebral disc that becomes degenerated may have to be partially or fully removed from a spinal column. Partial or full removal of an intervertebral disc may destabilize the spinal column. Destabilization of a spinal column may result in alteration of a natural separation distance between adjacent vertebrae. Maintaining the natural separation between vertebrae may prevent pressure from being applied to nerves that pass between vertebral bodies. Excessive pressure applied to the nerves may cause pain and/or nerve damage. During a spinal fixation procedure, a spinal implant may be inserted in a space created by the removal or partial removal of an intervertebral disc between adjacent vertebrae. The spinal implant may maintain the height of the spine and restore stability to the spine. Bone growth may fuse the implant to adjacent vertebrae.

A spinal implant may be inserted during a spinal fixation procedure using an anterior, lateral, posterior, or transverse spinal approach. A discectomy may be performed to remove or partially remove a defective or damaged intervertebral disc. The discectomy may create a space for one or more spinal implants. The amount of removed disc material may correspond to the size and type of the spinal implant or spinal implants to be inserted.

Spinal surgery may be complex due in part to the proximity of the spinal cord and/or the cauda equina. Preparation instruments and spinal implants may need to be carefully inserted to avoid damage to nerve tissue. Alignment and spacing of a spinal implant that is to be inserted into a patient may be determined before surgery. Achieving the predetermined alignment and spacing during surgery may be important to achieve optimal fusion of adjacent vertebrae.

U.S. Pat. No. 6,682,534 to Patel et al., which is incorporated by reference as if fully set forth herein, describes an endplate preparation instrument for preparing endplates of adjacent vertebral bodies. The instrument includes an elongated member that rotates in a housing member. The elongated member includes a cutting element that penetrates and removes bone from the endplates when the elongated member is rotated.

U.S. Pat. No. 6,599,294 to Fuss et al., which is incorporated by reference as if fully set forth herein, describes a surgical instrument for introducing a spinal implant between two vertebrae. The instrument includes two mutually opposing guide bodies. The guide bodies combine to form a guideway for lateral insertion of a spinal implant in the intervertebral space.

Some spinal implants may be inserted using a lateral (transverse) approach. U.S. patent application Ser. No. 10/633,371 to Mitchell et al., which is incorporated by reference as if fully set forth herein, describes spinal implants that may be inserted using a lateral (transverse) approach.

SUMMARY

An instrument may be used in a procedure to insert a spinal implant. In some embodiments, the spinal implant may be inserted into an intervertebral disc space. The spinal implant may provide stability and promote fusion of adjacent vertebrae. In an embodiment, an instrument may include a shaft assembly and an end member. The end member may rotate with respect to the shaft assembly. In some embodiments, an angle of the end member relative to the shaft assembly may be varied while the end member is in a disc space. The ability to rotate an end member relative to a shaft assembly may simplify and facilitate positioning of the end member at a desired location in the disc space. The ability to rotate the end member relative to the shaft assembly may decrease the size of an incision and opening needed to provide room for preparing a disc space and inserting a spinal implant in the disc space.

In certain embodiments, an instrument set for a spinal fusion procedure may include end members that are coupled to shaft assemblies such that separation of the end members from the shaft assemblies is inhibited. The end members may be coupled to the shaft assemblies by rivets, press fit connections, adhesives, or other fastening systems. An end member may be rotated and set in desired positions relative to a shaft assembly prior to insertion of the end member into a patient and during use of the end member.

In certain embodiments, an instrument set may include a shaft assembly and modular end members. Various end members may be removably coupled to the shaft assembly. The instrument set may include end members for various steps in a procedure for installing a spinal implant, such as disc preparation, disc space evaluation, and implantation.

In some instrument embodiments, an end member of an instrument may be separable from a shaft assembly of the instrument when the end member is placed in a selected orientation relative to the shaft assembly. An end member may include a slot. A portion of the shaft assembly may engage the slot to allow the end member to be selectively coupled to or separated from the shaft assembly.

In some instrument embodiments, a shaft assembly of an instrument may include a slide. The slide may engage an end member of the instrument to secure the end member at a selected angle with respect to the shaft assembly. The slide and the end member may include cooperative capture elements. The capture elements may engage to inhibit rotation of the end member with respect to the shaft assembly. In some embodiments, the capture elements may be frictional surfaces. In some embodiments, the capture elements include meshing teeth that form an interference fit to inhibit undesired rotation of the end member relative to the shaft assembly. The shaft assembly may include a locking member to lock a slide in position against an end member. In certain embodiments, a shaft assembly may include a biasing member to urge a slide into engagement with an end member.

In some embodiments, an end member of an instrument may be a rasp for abrading surfaces of vertebrae adjacent to a disc space. Upper and lower surfaces of the rasp may be textured to cut vertebral bone. In an embodiment, a surgeon may vary an angle of the rasp with respect to a shaft assembly while the rasp is in the disc space to selectively position the rasp relative to the vertebrae.

In certain embodiments, an end member of an instrument may be a trial member for evaluating a size and/or shape of a disc space. An instrument set may include trial members of various sizes that can be removably coupled to a shaft assembly. Sizes of the trial members may correspond to the sizes of implants available to a surgeon. In an embodiment, a surgeon may vary an angle of the trial member with respect to the shaft assembly to facilitate positioning of the trial member in the disc space.

In some embodiments, an end member of an instrument may be a tamp for positioning a spinal implant in a disc space. The tamp may include an end that engages the spinal implant to advance the spinal implant in the disc space. In an embodiment, a surgeon may vary an angle of the tamp with respect to a shaft assembly during insertion to facilitate positioning of the spinal implant in a desired location.

In certain embodiments, an angle of an end member relative to a shaft assembly may be controlled during a surgical procedure to allow a proximal end of a shaft assembly to be maintained in a relatively small range at an incision at a surface of the body. The angle of the end member relative to the shaft assembly may be adjusted at selected points of advancement of the instrument into a disc space. The angle of the end member relative to the shaft assembly may also be adjusted during removal of the end member from the disc space.

In some embodiments, an end member may be secured at a first angle relative to a shaft assembly. An end member may be moved to a first position along a path in a disc space while the end member is secured at the first angle. A capture element of the end member may be disengaged to allow the end member to rotate with respect to the shaft assembly. The angle of the end member with respect to the shaft assembly may be adjusted to a second angle. The end member may be secured to the shaft assembly at the second angle. The end member may be advanced to a second position on the path while the end member is secured at the second angle. The end member may be successively adjusted and advanced until the end member is in a desired position in the disc space.

BRIEF DESCRIPTION OF THE DRAWINGS

Advantages of the present invention will become apparent to those skilled in the art with the benefit of the following detailed description and upon reference to the accompanying drawings in which.

Figure 1:
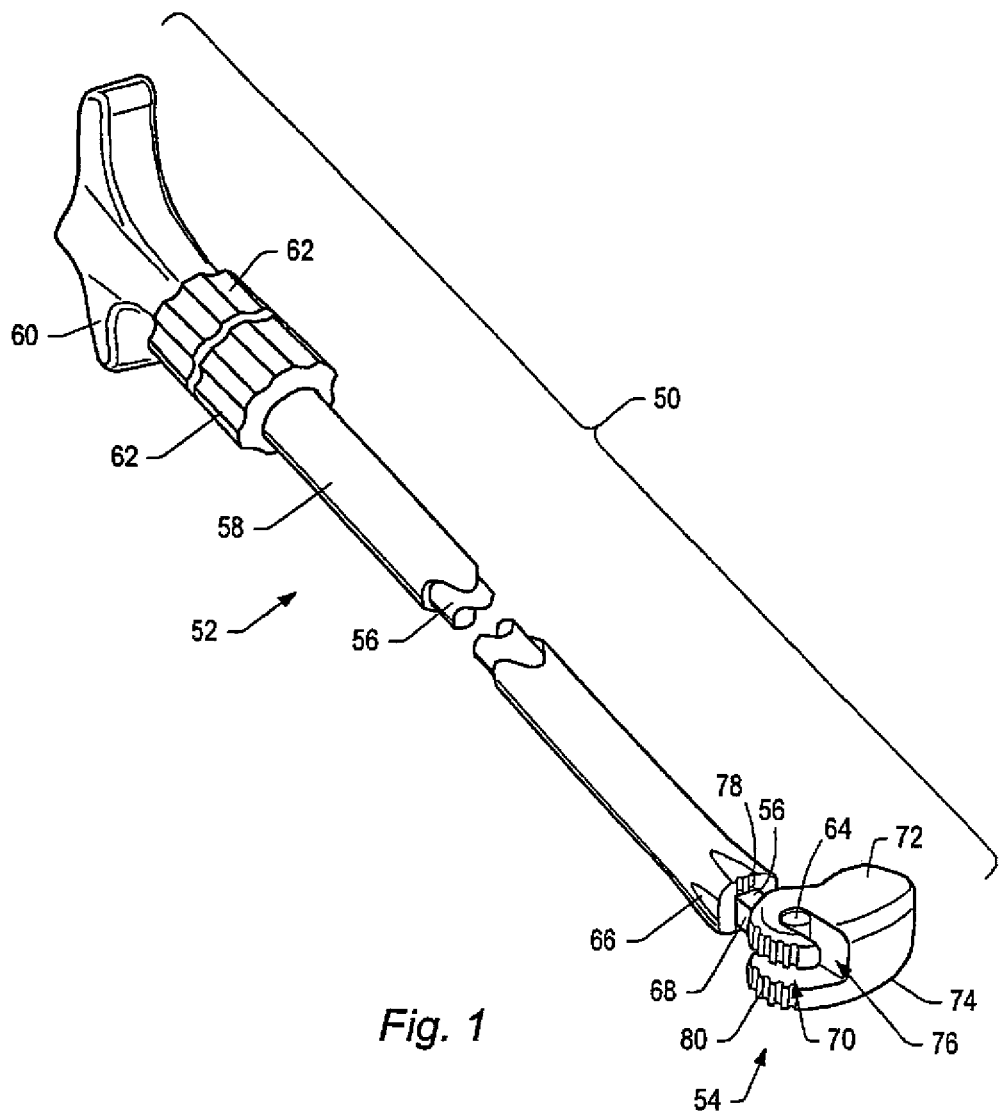
FIG. 1 depicts a perspective view of an embodiment of an instrument including a shaft assembly and a separable end member.

While the invention is susceptible to various modifications and alternative forms, specific embodiments thereof are shown by way of example in the drawings and will herein be described in detail. The drawings may not be to scale. It should be understood that the drawings and detailed description are not intended to limit the invention to the particular form disclosed, but on the contrary, the intention is to cover all modifications, equivalents, and alternatives falling within the spirit and scope of the present invention as defined by the appended claims.

DETAILED DESCRIPTION

An instrument may be used in a procedure to insert a spinal implant between human vertebrae. In an embodiment, the instrument may include a shaft assembly and an end member. The end member may rotate (e.g., pivot or angulate) with respect to the shaft assembly. The shaft assembly may include a slide that engages the end member to secure the end member at a selected angle with respect to the shaft assembly. To facilitate use of the instrument, the angle of the end member relative to the shaft assembly may be adjusted while the end member is in use in a patient.

Components of instruments may be made of materials including, but not limited to, metals, ceramics, and/or polymers. The metals may include, but are not limited to, stainless steel, titanium, and titanium alloys. Some components of instruments may be autoclaved and/or chemically sterilized. Components that may not be autoclaved and/or chemically sterilized may be made of sterile materials.

In some embodiments, an instrument may include end members that are coupled to shaft assemblies such that separation of the end members from the shaft assemblies is inhibited. The end members may be coupled to the shaft assemblies by rivets, press fit connections, adhesives, threaded connectors or other fastening systems. An end member may be rotated and set in desired positions relative to a shaft assembly prior to insertion of the end member into a patient and during use of the end member.

In some embodiments, an instrument set may include a shaft assembly and modular end members. The end members may be removably coupled to the shaft assembly. An instrument set may include different end members for various steps of a procedure, including, but not limited to, distraction, disc preparation, disc space evaluation, and implantation. End members used for disc preparation may include, but are not limited to, rasps, trials, chisels, curettes, or distractors. End members used for implantation may include, but are not limited to, inserters, tamps, or guides.

An instrument including an adjustable end member may allow preparation of a disc space and insertion of a spinal implant between human vertebrae to be effected from above an incision in a patient through a relatively small opening in the patient. The instrument may allow simple, efficient, and safe preparation of a disc space for receiving a spinal implant, including preparation of the contralateral (opposite) side of the disc space. The instrument may allow spinal implant insertion through a relatively small opening in the patient while maintaining maneuverability and visibility of the surgical site, spinal implant, and instruments during the procedure.

FIG. 1 depicts a perspective view of an embodiment of instrument 50. Instrument 50 may include shaft assembly 52 and end member 54. End member 54 may be pivotably coupled to shaft assembly 52. In some embodiments, end member 54 may be separable from shaft assembly 52. Shaft assembly 52 may be included in a modular instrument set having one or more end members.

Shaft assembly 52 may include shaft 56, slide 58, handle 60, locking member 62, and connector 64. Handle 60 may be coupled to shaft 56. In some embodiments, slide 58 of shaft assembly 52 is able to move longitudinally relative to shaft 56. A distal portion of slide 58 may engage an end member to inhibit undesired rotation of the end member relative to shaft 56. Locking member 62 may limit movement of shaft 56 relative to slide 58 to fix an angular position of an end member coupled to shaft assembly 52. As used herein, "slide" includes any element that moves (e.g., translates and/or rotates) with respect to another element. The slide may be positioned outside, inside, or along side the other element. A slide may be, but is not limited to, a shaft, a tube, a rod, a bar, a beam, or a combination thereof. In certain embodiments, a slide may threadably engage another element.

As shown in FIG. 1, slide 58 may be an outer shaft that surrounds a portion of shaft 56. Distal end 66 of slide 58 may engage end member 54 to hold the end member at a desired angle relative to shaft 56. Locking member 62 may be coupled to slide 58. Locking member 62 may be operated to control axial position of slide 58 relative to shaft 56. In some embodiments, locking member 62 may include a spring or other bias element that applies force to move slide 58 towards connector 64 of shaft 56.

In some embodiments, shaft 56 of instrument 50 may be a single member. In certain embodiments, a shaft may include multiple members. Distal portion 68 of shaft 56 may include connector 64. Connector 64 may be oriented perpendicular to a longitudinal axis of shaft 56. Connector 64 may form a "tee" shape in distal portion 68 of shaft 56.

End member 54 may include body opening 70, and surfaces 72, 74. End member 54 may be coupled to connector 64 of distal portion 68 of shaft 56. Pivoting end member 54 relative to shaft 56 about connector 64 may allow the end member to be positioned at various angles relative to the shaft during use of instrument 50. A rotational range of motion of end member 54 relative to shaft assembly 52 may be limited by a surface of the end member that defines opening 70. In some embodiments, the surface of the end member that defines opening 70 is a planar surface so that the range of motion of end member 54 relative to shaft assembly 52 is 180°. In other embodiments, the surface of the end member that defines opening 70 may be angled or curved so that the range of motion of end member 54 relative to shaft assembly 52 is less than or greater than 180°.

In some embodiments, end member 54 may be separable from shaft assembly 52. In certain embodiments, end member 54 may be separated from shaft assembly 52 when the end member is in a selected orientation with respect to the shaft assembly. For example, end member 54 may be separable from shaft assembly 52 when distal portion 68 of shaft 56 is aligned in slot 76. To separate end member 54 from shaft assembly 52, end member 54 may be rotated about connector 64 until distal portion 68 of shaft 56 is aligned in slot 76. Slide 58 may be retracted from connector 64, and end member 54 may be removed from distal portion 68.

In some embodiments, slide 58 and end member 54 may include complementary capture elements. As used herein, "capture element" includes any element that directly or indirectly contacts or engages another element to at least partially inhibit relative motion (e.g., translation, rotation) of the elements. A capture element may include, but is not limited to, a detent, a spring, a groove, a ridge, a tab, a pin, a projection, a slot, a hole, a notch, roughened or textured surfaces or threading. For example, as shown in FIG. 1, slide 58 may include teeth 78 and end member 54 may include complementary teeth 80. A capture element may be a separate component or may be a part of another element. In some embodiments, a captureelement may automatically release when a predetermined amount of force is applied to the element that is captured. In other embodiments, release of a capture element may require a separate action by a user (e.g., user actuated movement of the slide relative to the shaft).

Capture elements may be positioned over a subset of the range that end member 54 is able to rotate relative to shaft assembly 52 to define an instrument use range of the end member relative to the shaft assembly. In some embodiments, teeth 80 may be formed on end member 54 so that the instrument use range of the end member relative to the shaft assembly is from about 20° to about 180°, where 0° is the angle formed between the shaft assembly and the end member when a shaft of the shaft assembly is positioned in slot 76 such that the shaft assembly can be removed from the end member. In other embodiments, the instrument use range of the end member relative to the shaft assembly may be less or greater than the range of 20° to 180° (e.g., 30° to 180°, 10° to 180°, 10° to 190°, 45° to 135°).

In some embodiments, a slide of a shaft assembly may include detents or pins that engage holes or slots in an end member. In other embodiments, a slide of a shaft assembly may include holes or slots that engage detents or pins on an end member. In some embodiments, engaging surfaces of a slide and/or end member may be textured to inhibit relative motion between a shaft assembly and an end member when the slide is biased against the end member.

In an embodiment, turning (e.g., clockwise rotation) locking member 62 in a first direction (e.g., clockwise) may move slide 58 toward end member 54. Distal end 66 of slide 58 may engage end member 54. Turning locking member 62 in an opposite direction (e.g., counterclockwise) may move slide 58 away from end member 54. Distal end 66 of slide 58 may disengage from end member 54. With distal end 66 disengaged from end member 54, end member 54 may pivot with respect to shaft 56 about connector 64.

Figure 2:
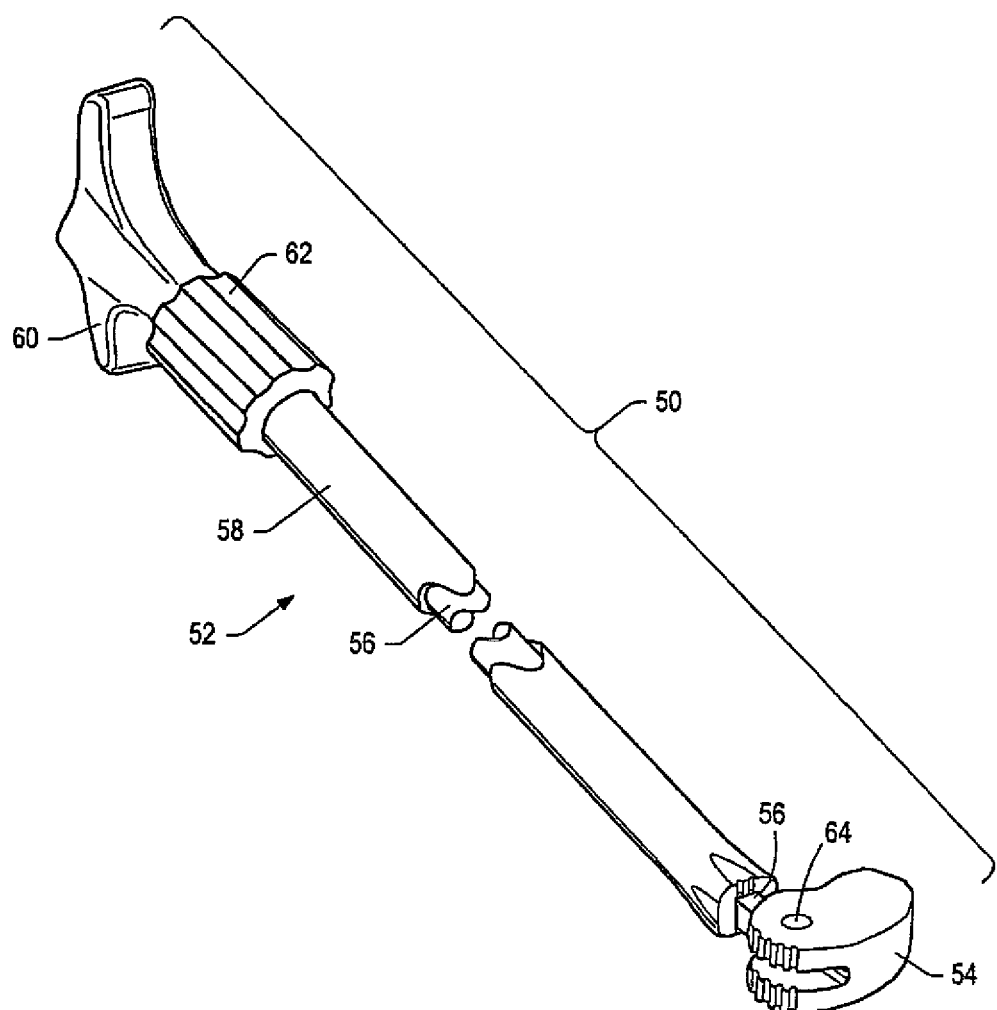
FIG. 2 depicts a perspective view of an embodiment of an instrument with a non-separable end member.

FIG. 2 depicts an embodiment of instrument 50 that has end member 54 fixed to shaft assembly 52. Connector 64 may be a pin that is press fit into end member 54. A portion of the pin passes through shaft 56 so that end member is able to rotate relative to shaft assembly 52 about connector 64. Locking member 62 may move slide 58 so that capture elements of the slide engage with, or disengage from, capture elements of end member 54.

Figure 3:
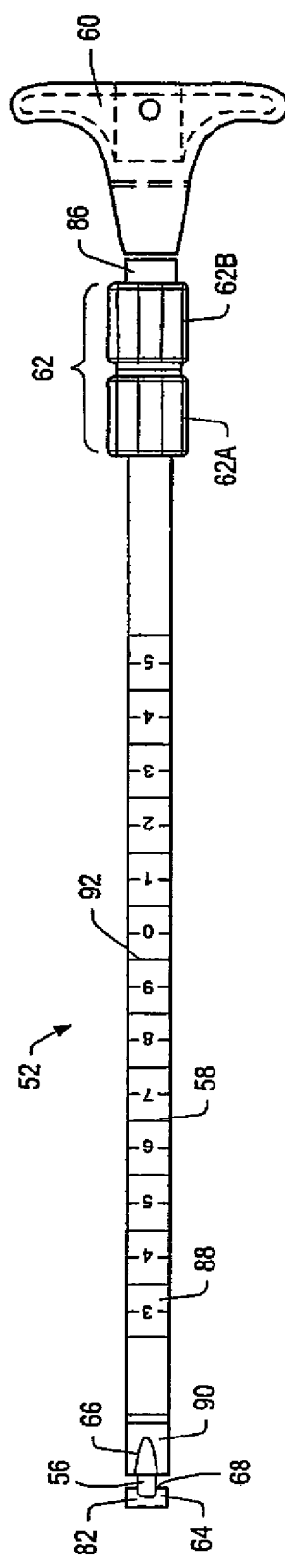
FIG. 3 depicts a front view of an embodiment of a shaft assembly.
Figure 4:
FIG. 4 depicts a side view of an embodiment of a shaft assembly.
Figure 5:
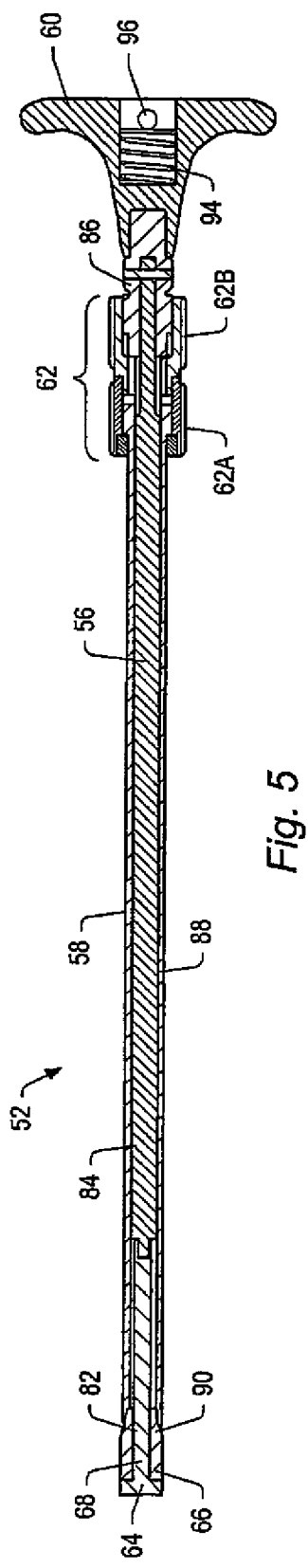
FIG. 5 depicts a cross-sectional view of the embodiment of the shaft assembly, taken substantially along line 5-5 of FIG. 4.

FIG. 3 and FIG. 4 depict front and side views of an embodiment of shaft assembly 52. FIG. 5 depicts a cross-sectional view of an embodiment of shaft assembly 52. Shaft 56 may include tip 82, body 84, and sleeve 86. Tip 82, body 84, and sleeve 86 may be coupled by various methods including, but not limited to, application of an adhesive, welding, press-fitting, threading, pins, and/or rivets. Tip 82 may have an elongated section and connector 64. A cross-sectional shape of the elongated section perpendicular to the longitudinal axis of the elongated section may be substantially square. Handle 60 may be coupled to sleeve 86 and shaft 56 by a pin.

Slide 58 may include tube 88 and collar 90. In some embodiments, tube 88 may have a substantially cylindrical outer surface. An opening through collar 90 may have a substantially square shape that corresponds to a shape of the elongated section of tip 82. The shape of the opening in collar 90 and the shape of the elongated section of tip 82 may inhibit rotation of slide 58 relative to shaft 56.

Slide 58 may include indicia 92. Indicia 92 may indicate insertion depth of an end member into a patient.

Handle 60 may be used to hold shaft assembly 52. In some embodiments, locking member 62 may be rotated with fingers of the same hand with which a user is holding handle 60. A top of handle 60 may be an impact surface. A mallet or other impact instrument may strike the impact surface to drive an end member coupled to the shaft assembly into a disc space. As shown in FIG. 5, some embodiments of handle 60 may include spring 94 and pin 96. An end of a slap hammer may include a keyway that engages pin 96 to couple the slap hammer to shaft assembly 52. Spring 94 may apply force to the slap hammer that holds the shaft assembly and the slap hammer together. The slap hammer may be used to remove an end member from a disc space.

Figure 6:
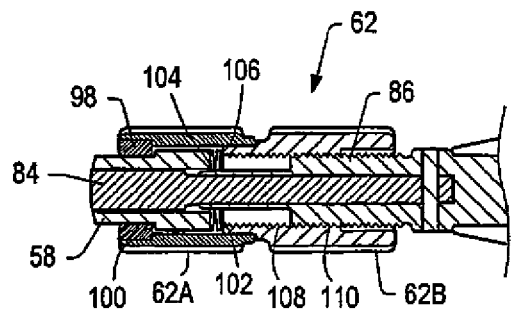
FIG. 6 depicts a detail view of the embodiment of the locking member shown in FIG. 5.

FIG. 6 depicts a detail view of an embodiment of locking member 62. Locking member 62 may include portions 62A and 62B. Portions 62A and 62B may be fixedly coupled (e.g., by adhesive, welding, threads, or soldering) after the portions are properly positioned relative to shaft 56 and slide 58. Capture washer 98 may be coupled to a distal end of portion 62A. Capture washer 98 may engage rim 100 of slide 58 when locking member 62 is rotated to move the slide away from a connector of the shaft assembly. Belleville washers 102 may be positioned between end face 104 of slide 58 and end face 106 of portion 62B. When locking member 62 is rotated to move slide 58 towards connector 64 (depicted in FIGS. 3-5), end face 106 may push against Belleville washers 102. Belleville washers 102 may push against slide 58 to move the slide towards the connector.

Threading 108 on portion 62B may mate with threading 110 of sleeve 86. Locking member 62 may be rotated in a first direction to move slide 58 towards a connector of a shaft assembly. Teeth of the slide may engage teeth of an end member to fix the angular position of the end member relative to the shaft assembly. Locking member 62 may be rotated in an opposite direction to move slide 58 away from the connector. When the slide is moved away from the connector, teeth of the slide may disengage from teeth of the end member to allow the angular position of the end member relative to the shaft to be changed.

To assemble shaft assembly 52 (depicted in FIGS. 3-5), collar 90 may be placed on tip 82. Tip 82 may be welded to body 84. Retainer washer 98 may be welded to portion 62A. Portion 62A may be placed on tube 88. Tube 88 may be welded to collar 90.

Sleeve 86 may be press-fit into handle 60. Portion 62B may be threaded onto thread 110 of sleeve 86. Belleville washers may be placed about shaft 56. An opening in sleeve 86 may be aligned with an opening in shaft 56 and a pin may be press fit into the openings to couple the sleeve and handle 60 to the shaft. Portion 62A may be positioned against portion 62B. Portion 62A and portion 62B may be welded together to form locking member 62 and the complete shaft assembly.

Figure 7:
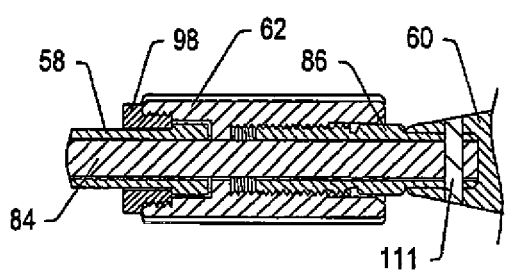
FIG. 7 depicts a detail view of an embodiment of a locking mechanism.

FIG. 7 depicts a cross-sectional view of a portion of an embodiment of a shaft assembly. Capture washer 98 may be positioned on slide 58. A tip may be placed in a collar. The tip may be coupled to a body. The body may be positioned in slide 58. The collar may be coupled to slide 58. Locking member 62 may be positioned on slide 58. An adhesive (e.g., Loctite Engineering Adhesive) may be applied to threading of capture washer 98. Capture washer 98 may be threaded on locking member 62. Sleeve 86 may be press fit in handle 60 so that an opening through the sleeve aligns with an opening through the handle. Sleeve 86 may be threaded in locking member 62 until an opening in body 84 aligns with the openings through the sleeve and handle 60. Pin 111 may be positioned in handle to fix the position of body 84 relative to sleeve 86 and handle 60. Rotating locking member 62 advances or retracts slide 58 relative to handle 60.

Figure 8:
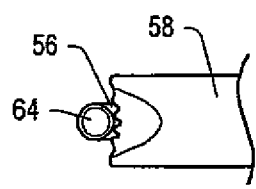
FIG. 8 depicts a detail view of an embodiment of a distal portion of a shaft assembly in a closed position.
Figure 9:
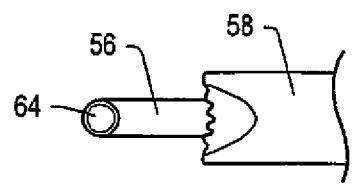
FIG. 9 depicts a detail view of an embodiment of a distal portion of a shaft assembly in an open position.

FIG. 8 depicts a distal portion of a shaft assembly when a locking member of the shaft assembly is rotated to drive slide 58 towards connector 64 of shaft 56. FIG. 9 depicts a distal portion of an embodiment of a shaft assembly when the locking member of the shaft assembly is disengaged to drive slide 58 away from connector 64 of shaft 56.

Figure 10:
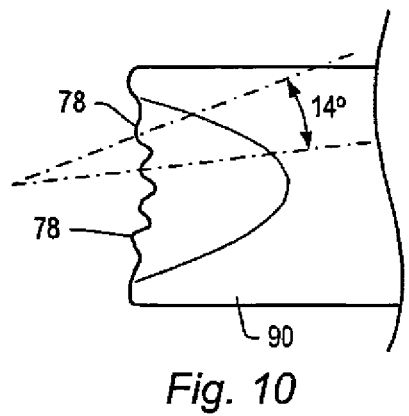
FIG. 10 depicts a detail view of an embodiment of teeth on a collar of a shaft.

FIG. 10 depicts a detail view of an embodiment of teeth 78 of collar 90 of a slide. In some embodiments, collar 90 may include from 1 to about 8 teeth 78. In an embodiment, collar 90 includes 4 teeth. In some embodiments, an angular spacing between teeth 78 may be from about 5 to about 30°. In an embodiment, the angular spacing between teeth is about 14°. In some embodiments, an angle between sides of tooth 78 may be from about 150° to about 5°. In an embodiment, the angle between sides of a tooth is about 60°.

Figure 11:
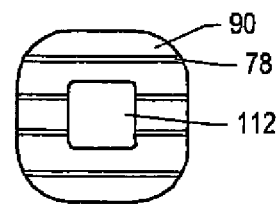
FIG. 11 depicts an end view of an embodiment of a collar of a shaft.

FIG. 11 depicts an end view of an embodiment of a collar of a slide. Opening 112 may receive a tip of a shaft of a shaft assembly. In some embodiments, opening 112 may have a shape other than square or rectangular, such as, but not limited to, circular, diamond-shaped, or hexagonal. A slide of an instrument may translate on a shaft without rotation of the slide relative to the shaft. Engaging surfaces of the shaft and the collar may inhibit rotation of the shaft with respect to the collar. If a shape of an opening of the collar is circular, a shaft positioned in the collar may include a slot. A pin may be press fit into the slide through the slot so that rotation of the shaft relative to the slide is inhibited, while still allowing for axial movement of the slide relative to the shaft.

Figure 12:
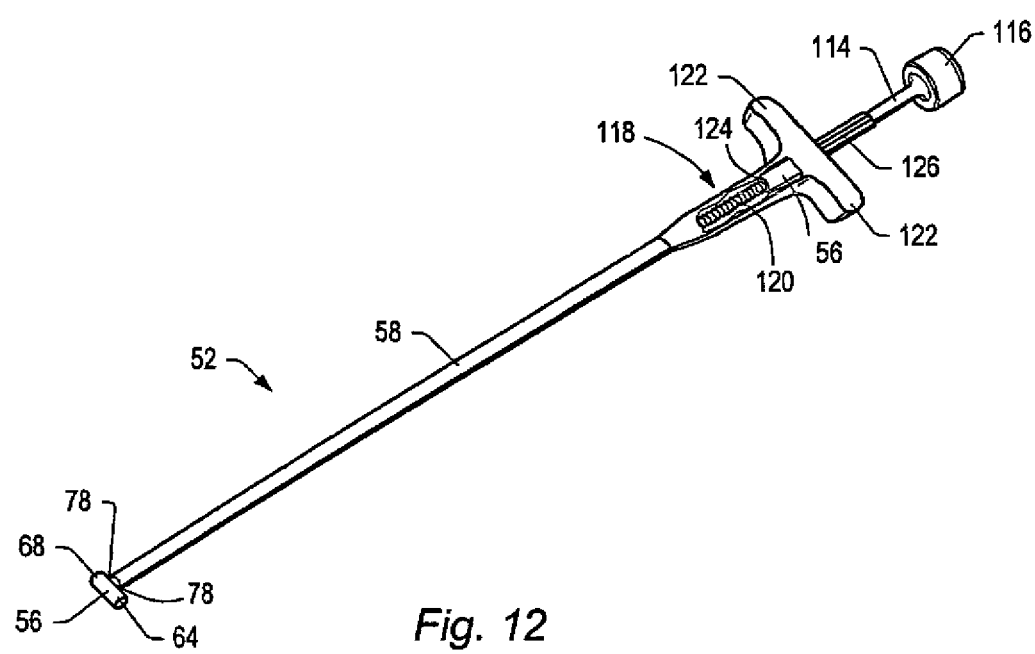
FIG. 12 depicts a perspective view an embodiment of a shaft assembly with a portion of a bias section of the shaft assembly shown in cut-away to show a biasing member of the shaft assembly.

In an embodiment, a shaft assembly may include a biasing member that urges a slide toward a distal portion of a shaft assembly. A biasing member may include, but is not limited to, a coil spring, Belleville washers, or an elastomeric member. FIG. 12 depicts shaft assembly 52 including shaft 56 and slide 58. Shaft 56 may include a distal portion and a proximal portion. Distal portion 68 may include connector 64. Proximal portion 114 may include knob 116. Knob 116 may be an impact surface that allows an end member that is coupled to connector 64 to be driven into a disc space. Knob 116 may also be positioned against a user's palm or thumb during use to allow a user to move slide 58 relative to shaft 56.

Shaft assembly 52 may include bias section 118. A portion of bias section 118 of FIG. 12 is shown in cut-away to reveal some of the inner features of the bias section. Bias section 118 may include biasing member 120, and grips 122. A first end of biasing member 120 may be positioned against a portion of bias section 118. A second end of biasing member 120 may be positioned against ledge 124 of shaft 56. In some embodiments, ledge 124 may be formed by reducing a diameter of a portion of shaft 56. In some embodiments, a ledge may be formed by placing a weld bead or other obstruction on the shaft. In some embodiments, a ledge may be formed by a pin or washer coupled to the shaft. Biasing member 120 may provide a force to slide 58 that moves the slide towards connector 64 of shaft 56. A user may grasp grips 122 with fingers while knob 116 is positioned against the user's palm or thumb. Grips 122 may be pulled away from connector 64 to move slide 58 away from the connector. When grips 122 are released, biasing member 120 may move slide 58 towards connector 64.

An end member may be coupled to connector 64. Teeth 78 may engage portions of the end member to set a desired angle of the end member relative to shaft assembly 52. The angle of the end member relative to the shaft assembly may be adjusted during use by repositioning slide 58 relative to the end member.

In some embodiments, shaft assembly 52 may include lock 126, Lock 126 may include thread that complements a threaded portion of shaft 56. When an end member that is coupled to connector 64 is at a desired angle relative to shaft assembly 52, lock 126 may be rotated to position an end of the locking member against bias section 118. Positioning locking member 126 against biasing section 118 may inhibit movement of slide 58 relative to the end member, thus inhibiting rotation of the end member relative to shaft assembly 52. When it is desired to change the angle of shaft assembly 52 relative to the end member, locking member 126 may be rotated to move the locking member away from bias section 118 so that slide 58 can be moved to allow the teeth of the slide to be repositioned with respect to the end member.

Figure 13:
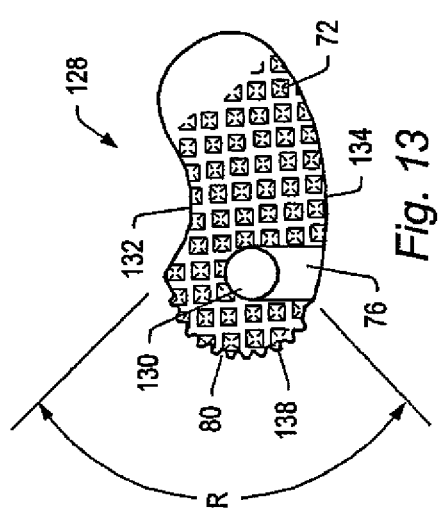
FIG. 13 depicts a top view of an embodiment of a rasp.
Figure 14:
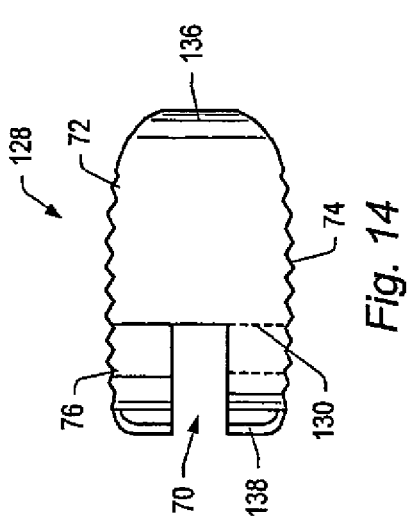
FIG. 14 depicts a front view of an embodiment of a rasp.

In an embodiment, an end member may be a rasp that is used to abrade surfaces of vertebrae. FIGS. 13 and 14 depict top and front views, respectively, of rasp 128. Rasp 128 may include opening 70, slot 76, and hole 130. Rasp 128 may couple with a shaft of a shaft assembly. Hole 130 may receive a portion of a connector of the shaft. Opening 70 may allow rasp 128 to pivot relative to the shaft of the shaft assembly.

Rasp 128 may include posterior side 132 and anterior side 134. Sides 132, 134 may be curved, Sides 132, 134 may have substantially the same curvature as a spinal implant to be inserted in a disc space formed using the rasp. In some embodiments, the curvature of posterior side 132 may be substantially the same as the curvature of anterior side 134. In some embodiments, the curvature of posterior side 132 may be different than the curvature of anterior side 134. In some embodiments, posterior side 132 may have a smaller radius of curvature than anterior side 134. In some embodiments, posterior side 132 and/or anterior side 134 may include no significant curvature.

Distal end 136 of rasp 128 may be tapered and/or curved. Tapered and/or curved surfaces of distal end 136 may facilitate insertion of rasp 128 in a disc space. In some embodiments, the tapered and/or curved surfaces of distal end 136 may be textured. The textured surface may facilitate removal of intervertebral disc material during use. In some embodiments, distal end 136 may not be tapered and/or curved. Proximal end 138 of rasp 128 may be blunt and/or rounded. In some embodiments, upper surface 72 and lower surface 74 of rasp 128 may be angled relative to each other. Angled upper surface 72 and lower surface 74 may facilitate removal of intervertebral disc material during use.

Upper surface 72 and lower surface 74 of rasp 128 may be textured to abrade and/or cut vertebral bone. Texturing may be provided by methods including, but not limited to, sanding the surface, forming grooves in the surface, shot peening the surface, scoring the surface using an electrical discharge process, and/or embedding hard particles in the surface.

Rasp 128 may include teeth 80. Teeth 80 may engage cooperating elements of a slide of a shaft assembly to secure a position of rasp 128 relative to the shaft. Teeth 80 may allow an angle of rasp 128 relative to a shaft to be selectively set in range R. In some embodiments, range R may be at least about 90°. In some embodiments, range R may be about 150°, about 120°, about 90°, or about 45°. Slot 76 may allow rasp 128 to be separated from the shaft assembly when a portion of the shaft is aligned with slot 76. Slot 76 may be located on rasp 128 such that the portion of the shaft cannot be aligned with slot 76 when the rasp is positioned between vertebrae in a patient.

Figure 15:
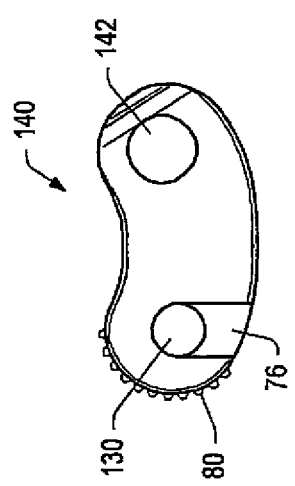
FIG. 15 depicts a top view of an embodiment of a trial member.
Figure 16:
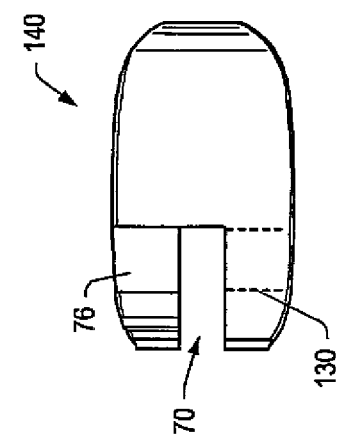
FIG. 16 depicts a front view of an embodiment of a trial member.

In an embodiment, an end member may be a trial member used to evaluate size and/or shape of a disc space. FIGS. 15 and 16 depict top and front views, respectively, of trial member 140. Trial member 140 may include various tapered, curved and/or flat outer surfaces. Trial member 140 may include opening 70, slot 76, and hole 130 that allow the trial member to be removably coupled to a shaft of a shaft assembly. Slot 76 may be located on trial member 140 such that the shaft of the shaft assembly cannot be aligned with slot 76 when the trial member is positioned between vertebrae in a patient. Trial member 140 may include teeth 80. Teeth 80 may allow the trial member to be set at a desired angle relative to the shaft of the shaft assembly. Trial member 140 may include marker 142. Marker 142 may be color coded or include indicia to indicate to which instrument set the trial belongs.

An instrument set may include trial members of various sizes. The instrument set may include a trial member for each spinal implant size included in the instrument set. In some embodiments, a trial member may have the same dimensions as the dimensions of a corresponding spinal implant. In some embodiments, one or more dimensions of a trial member may differ from those of a corresponding spinal implant. For example, a height of each trial member may be undersized relative to a height of a corresponding spinal implant for each trial.

Figure 17:
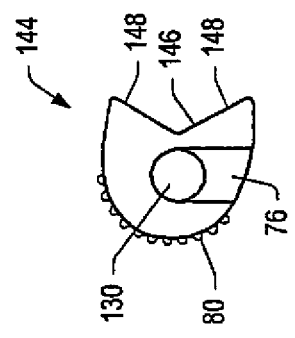
FIG. 17 depicts a top view of an embodiment of a tamp.
Figure 18:
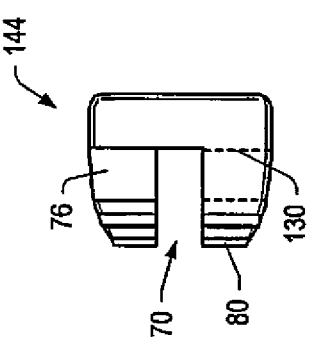
FIG. 18 depicts a front view of an embodiment of a tamp.

In an embodiment, an end member may be a tamp used to position a spinal implant in a disc space. FIGS. 17 and 18 depict top and front views, respectively, of tamp 144. Tamp 144 may include opening 70, slot 76, and hole 130 that allow the tamp to be removably coupled to a shaft of a shaft assembly. Slot 76 may be located on tamp 144 such that the shaft of the shaft assembly cannot be aligned with slot 76 when the tamp is positioned between vertebrae in a patient. Tamp 144 may include teeth 80 that allow the tamp to be set at a desired angle relative to the shaft of the shaft assembly. Tamp 144 may include end face 146 and tips 148. End face 146 may contact a spinal implant that is partially inserted into a disc space. An instrument formed of a shaft assembly and tamp 144 may be pushed or impacted with a mallet to advance the spinal implant into a desired position in a disc space.

End face 146 may include any of a variety of profiles, including, but not limited to, flat, convex, concave, arcuate, wedge-shaped, u-shaped, or vee-shaped. End face 146 may have various surface contours, including, but not limited to, smooth, textured, or padded. In certain embodiments, a tamp may include elements such as tabs, pins, or protrusions for engaging a portion of a spinal implant. Such elements may facilitate manipulation of the spinal implant with the tamp. For example, tips 148 (shown in FIG. 17) on tamp 144 may engage a groove or notch on a spinal implant to facilitate placement of the spinal implant using the tamp.

Figure 19A:
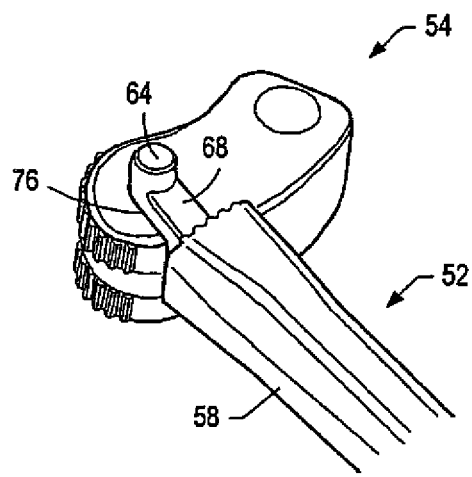
FIGS. 19A-19D depict schematic representations of installation of an end member onto a shaft assembly.
Figure 19B:
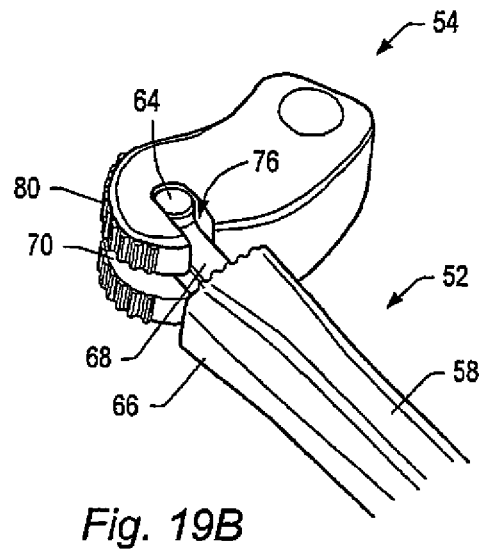
Figure 19C:
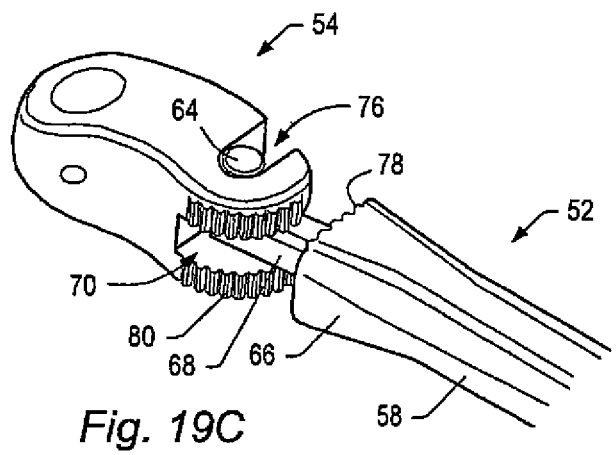
Figure 19D:
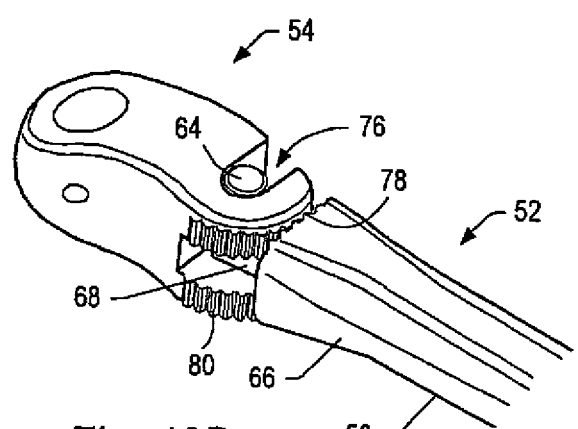

FIGS. 19A-19D depict coupling of end member 54 with shaft assembly 52. Pin 64 may be aligned with hole 130 (shown in FIGS. 13-18). As depicted in FIG. 19A, distal portion 68 of shaft 56 may be aligned with slot 76. Pin 64 and distal portion 68 may be placed in slot 76. FIG. 19B depicts pin 64 may engaged with hole 130 (shown in FIGS. 13-18). End member 54 may be pivoted about pin 64. As depicted in FIG. 19C, distal portion 68 of shaft 56 may be positioned in opening 70 away from slot 76. Slide 58 may be translated toward end member 54. As depicted in FIG. 19D, teeth 78 on distal end 66 of slide 58 may engage teeth 80 of end member 54. Engagement of teeth 78, 80 may inhibit rotation of end member 54 relative to shaft assembly 52.

In an embodiment, an instrument may be used in a procedure to insert a spinal implant in a disc space between adjacent vertebrae. The spinal implant may replace all or a portion of an intervertebral disc that has degenerated due to wear, trauma, and/or disease. The spinal implant may restore a normal separation distance between adjacent vertebrae and promote fusion of the vertebrae. In certain embodiments, a spinal implant may be inserted in a space formed between two portions of a bone to extend the length of the bone.

A discectomy may be performed to remove disc material from a disc space. A distractor may be positioned in the disc space to establish a separation distance between the vertebrae. A disc space may be prepared using instruments such as, but not limited to, scalpels, drills, curettes, chisels, or rongeurs. A chisel may be used to remove portions of vertebral bone and form channels in the vertebral endplates adjacent to the disc space.

In some embodiments, an angle of an end member relative to a shaft assembly may be adjusted while the end member is in a disc space. Pivoting the end member may facilitate positioning of the end member in various regions of the disc space. The ability to pivot an end member may allow a user to maintain the shaft assembly of an instrument in a desired range without requiring a large working space. For example, an angle of the end member relative to the shaft assembly may be controlled such that a position of the shaft assembly is maintained in a relatively small range within a surgical opening in the patient at a surface of the body as the end member is advanced in the disc space. The angle may be adjusted at selected points of advancement of the instrument into and/or withdrawal of the instrument from a disc space. In one embodiment, an angle of an end member with respect to a shaft assembly is adjusted twice during advancement of the end member and twice during withdrawal of the end member. In other embodiments, an angle of the end member with respect to the shaft assembly is adjusted three or more times during advancement of the end member and three and/or more times during withdrawal of the end member.

In some embodiments, an end member may be allowed to pivot freely relative to the shaft assembly as the end member is withdrawn from an incision. The end member may deflect as the end member encounters tissue during withdrawal. Pivoting of an end member during withdrawal may reduce damage to tissue that might occur if the end member were locked at a fixed angle during withdrawal of the end member.

Vertebral surfaces may require preparation before insertion of a spinal implant in a disc space. A rasp may be inserted in an intervertebral disc space from a posterior or transverse approach to abrade vertebral surfaces. Vertebral surfaces may be abraded to remove osteophytes and/or to smooth rough surfaces. In some embodiments, an instrument with an end member that is a rasp may be used to roughen vertebral endplates. Roughening of vertebral endplates may initiate a healing response that promotes bone growth. The bone growth may promote fusion of adjacent vertebrae with an installed spinal implant.

In an embodiment, an instrument including a rasp may be used to prepare a disc space for a spinal implant. An angle of the rasp with respect to a shaft assembly of the instrument may be adjusted to facilitate positioning of the rasp in the disc space. FIGS. 20A-20E depict use of instrument 50 including rasp 128. Rasp 128 may be placed in disc space 150 at various angles relative to shaft assembly 52 of instrument 50. Vertebral surfaces may be abraded by moving shaft assembly 52 back and forth with rasp 128 in disc space 150.

An angle of rasp 128 relative to shaft assembly 52 may be selected to allow rasp 128 to be inserted in disc space 150 during a transverse approach. After insertion, an angle of rasp 128 relative to shaft assembly 52 may be adjusted to allow instrument 50 to be positioned and used at different locations within disc space 150, including but not limited to the area across midline of the vertebral body. Shaft assembly 52 may be pivoted relative to rasp 128 by moving a slide of the shaft assembly and angling the shaft assembly relative to rasp 128. After a desired angle is obtained, the slide may be moved against rasp 128 to secure the position of the rasp relative to shaft assembly 52. Rasp 128 may be forced against an endplate of a first vertebra. Rasp 128 may be moved to treat the vertebral surface of the first vertebra. Rasp 128 may be forced against the endplate of a second vertebra. Rasp 128 may be moved to treat the vertebral surface of the second vertebra.

Figure 20A:
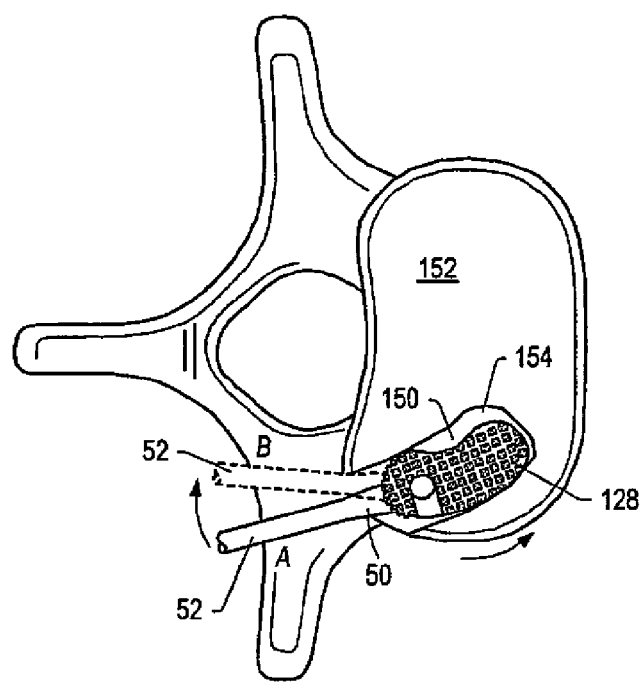
FIGS. 20A-20E depict-schematic representations of use of a rasp to prepare a disc space.
Figure 20B:
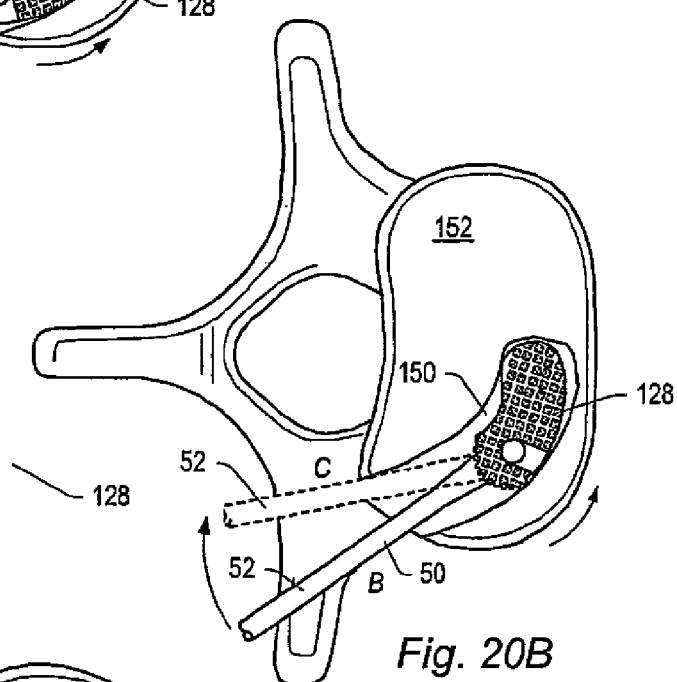
Figure 20C:
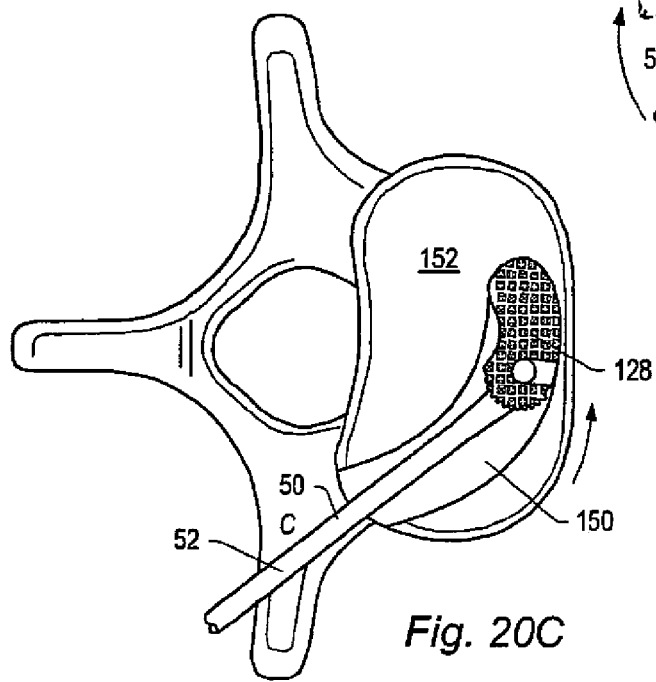

A discectomy may be performed to remove a portion of an intervertebral disc. The discectomy may form an initial path between vertebrae. After formation of the initial path, rasp 128 may be used to extend the path in a desired trajectory. Referring to FIG. 20A, rasp 128 may be initially secured in first orientation A relative to shaft assembly 52. Rasp 128 may be advanced in disc space 150 in an initial space formed during a discectomy. With rasp 128 in disc space 150, shaft assembly 52 may be adjusted from orientation A to orientation B. Frictional engagement of rasp 128 with adjacent disc 152 may stabilize rasp 128 sufficiently to allow shaft assembly 52 to be angled by moving a slide of the shaft assembly and angling the shaft assembly. After obtaining desired angle B, the slide may be moved so that the slide engages capture members of rasp 128. Rasp 128 may be used to extend disc space 150 formed between vertebrae. FIG. 20B depicts a representation of disc 152 after rasp 128 has been used to extend disc space 150. Shaft assembly 52 may be adjusted from orientation B to orientation C. Rasp 128 may be further advanced into disc into 152 to establish desired disc space 150, as depicted in FIG. 20C.

Figure 20D:
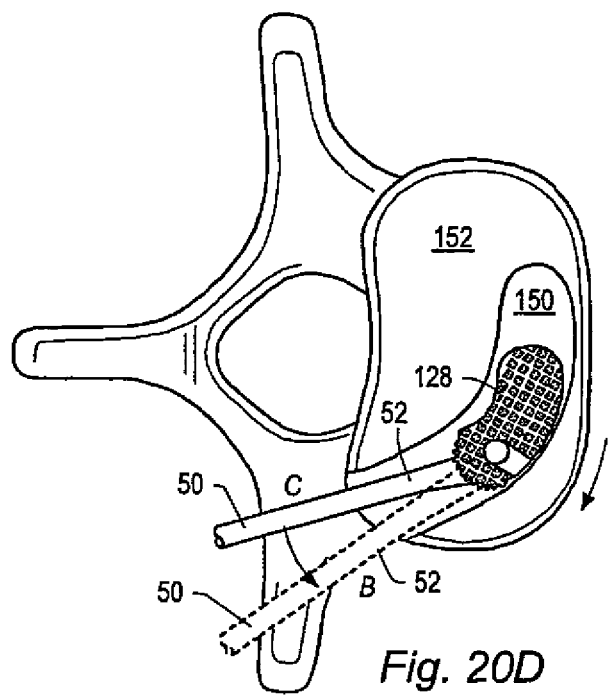
Figure 20E:
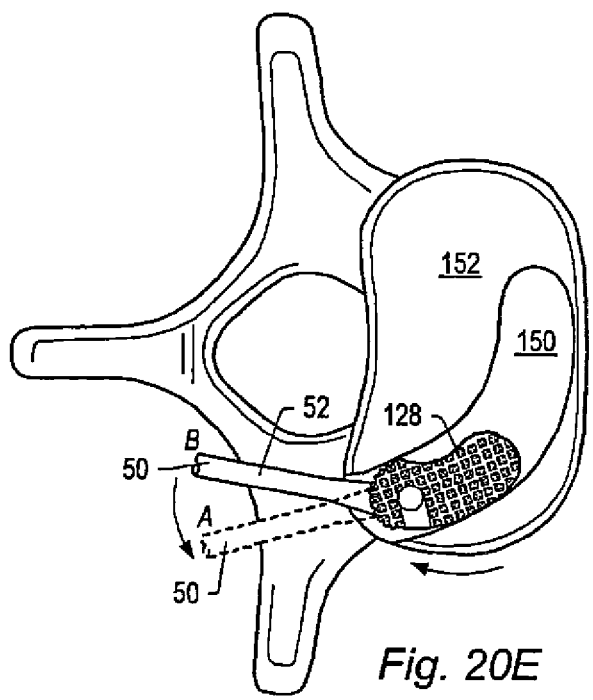

Instrument 50 may be removed from disc space 150 by reversing the steps used for insertion of the instrument. For example, with shaft assembly 52 at orientation C, rasp 128 may be partially withdrawn from disc space 150 (FIG. 20D). Shaft assembly 52 may be adjusted to orientation B. Rasp 128 may be further withdrawn from disc space 150 (FIG. 20E). Shaft assembly 52 may be adjusted to orientation A, and instrument 50 may be removed from the incision.

In an embodiment, an instrument including a trial member may be used to gauge a disc space before insertion of a spinal implant. In an insertion procedure that uses modular end members, a rasp may be removed from a shaft assembly after a disc space is prepared. A trial may be attached to the shaft assembly. The instrument with the trial attached may be inserted into the disc space. The trial may have the same outer shape as the shape of a spinal implant in an instrumentation set provided for the spinal implant insertion procedure. If the trial is easily inserted into the disc space, the corresponding spinal implant may not have sufficient height. If the trial cannot be inserted, the corresponding spinal implant may have too much height. Insertion of the trial should be achieved with some impact on an end of the shaft assembly. The trial may be fully inserted along the established disc space to ensure that the corresponding spinal implant will be able to follow the same path. The angle of the shaft assembly relative to the trial may be adjusted during insertion of the trial into the disc space. After complete insertion, the trial may be removed from the disc space.

Figure 21A:
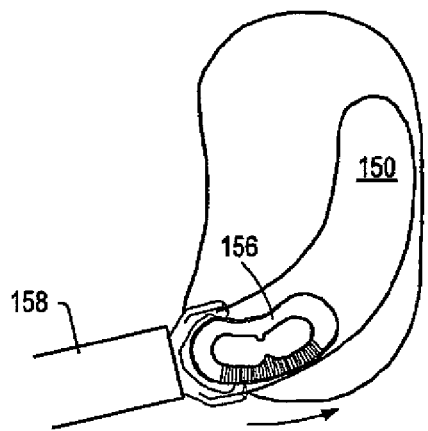
FIGS. 21A-21D depict schematic representations of use of a tamp to position a spinal implant in a disc space.

In an embodiment, an instrument may be used to position, guide, and/or manipulate a spinal implant in a disc space. FIGS. 21A-21D depict positioning of spinal implant 156 in disc space 150. In some embodiments, bone growth promoting material may be placed in the disc space and/or in openings in the spinal implant to minimize or eliminate gaps between the spinal implant and walls defining the disc space. The bone growth promoting material may be, but is not limited to, autologous bone, allograft bone, xenograft bone, calcium phosphates, collagen, calcium sulfates, demineralized bone matrix, bone morphogenetic proteins, platelet derived growth factors, bone marrow aspirate, and/or blood. Spinal implant 156 may be placed in an initial position in disc space 150 using a spinal implant inserter 158 (FIG. 21A).

Figure 21B:
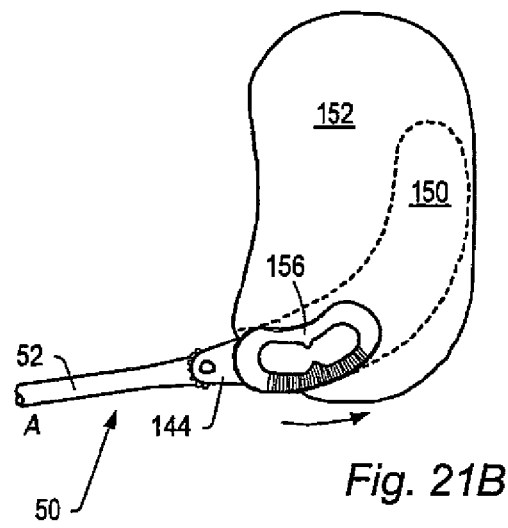
Figure 21C:
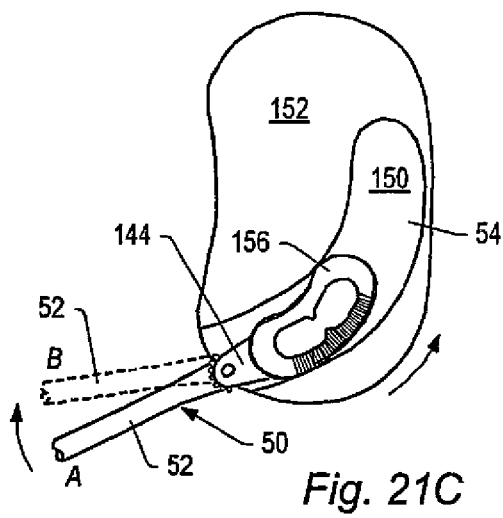
Figure 21D:
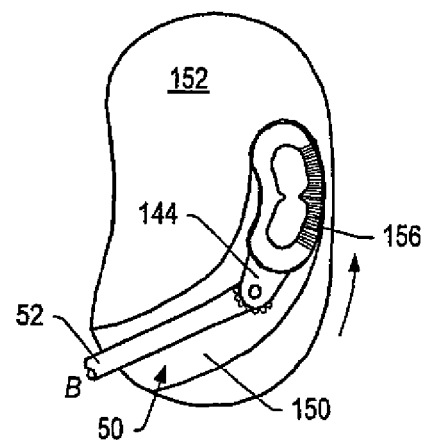

As depicted in FIG. 21B, instrument 50 with tamp 144 and shaft assembly 52 may be coupled to spinal implant 156. Tamp 144 may be angled relative to shaft assembly 52 in orientation A. Shaft assembly 52 may be advanced to drive tamp 144 and spinal implant 156 in disc space 150 (FIG. 21C). In certain embodiments, a mallet may be used to strike shaft assembly 52 of instrument 50 to advance spinal implant 156 in disc space 150.

Shaft assembly 52 may be changed from orientation A to orientation B while tamp 144 remains in place in disc space 150. In some embodiments, instrument 50 may be withdrawn slightly from spinal implant 156 to facilitate angular adjustment. Tamp 144 may be secured to shaft assembly 52 when the tamp is positioned in orientation B. Instrument 50 may be used to further advance spinal implant 156 into disc space 150. Tamp 144 may be used to push spinal implant 156 fully into disc space 150. A position of spinal implant 156 may be monitored using radiological techniques. After full insertion of spinal implant 156, instrument 50 may be withdrawn from the surgical site.

In this patent, certain U.S. patents have been incorporated by reference. The text of such U.S. patents is, however, only incorporated by reference to the extent that no conflict exists between such text and the other statements and drawings set forth herein. In the event of such conflict, then any such conflicting text in such incorporated by reference in such U.S. patents is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. A system for inserting a spinal implant in a patient, comprising:
   a shaft;
   a coupling member rotatably coupled with the shaft, wherein the coupling member has an end face with one or more elements configured to engage and insert an implant between vertebrae, wherein the coupling member is configured to be removed from the patient after inserting the implant; and
   a slide slideably disposed over and coupled to the shaft, the slide being axially moveable between a first position spaced from the coupling member and a second position coupled to the coupling member;
   wherein the slide is configured to selectively couple with the coupling member to inhibit rotation of the coupling member with respect to the shaft, wherein the shaft and the coupling member are configured to remain coupled when the slide is in the first position,
   wherein the slide comprises one or more capture elements, wherein the coupling member comprises one or more capture elements, the one or more capture elements of the coupling member comprising teeth, and wherein at least one capture element of the slide is configured to selectively couple with at least one capture element of the coupling member to inhibit rotation of the coupling member with respect to the shaft.

2. The system of claim 1, wherein the coupling member is separable from the shaft when the coupling member is placed in a selected orientation with respect to the shaft.

3. The system of claim 1, wherein the one or more capture elements of the coupling member and the capture elements of the slide are configured to selectively inhibit rotation of the coupling member with respect to the shaft over a range of at least 90°.

4. The system of claim 1, further comprising a locking member coupled to the slide, wherein the locking member is configurable to lock the coupling member relative to the shaft.

5. The system of claim 1, further comprising a biasing member coupled to the slide, wherein the biasing member is configured to urge the slide toward the coupling member.

6. The system of claim 1, wherein the slide is configured to selectively couple with the coupling member to inhibit rotation of the coupling member at selected positions between a first position and a second position.

7. The system of claim 6, wherein the slide is configured to selectively couple with the coupling member to inhibit rotation of the coupling member in at least three positions between the first position and the second position with respect to the shaft.

8. A system for inserting a spinal implant in a patient, comprising:
   a shaft; and
   a coupling member configured to rotatably directly couple with the shaft, wherein the coupling member has an end face with one or more elements configured to engage and insert an implant between vertebrae, wherein the coupling member is configured to be removed from the patient after inserting the implant;

wherein the shaft and coupling member are configured to be directly coupled such that the shaft may be moved from a first angle with respect to the coupling member to a second angle with respect to the coupling member while the shaft and coupling member remain directly coupled and while the coupling member is positioned between vertebrae;

wherein the coupling member is removable from the shaft by placing the coupling member at a selected angle with respect to the shaft.

9. The system of claim 8, wherein the coupling member comprises a slot, wherein a portion of the shaft is configured to pass through the slot when the coupling member is rotated to a selected angle to allow the coupling member to be removed from the shaft.

10. The system of claim 9, wherein the coupling member comprises a surface configured to face an endplate of a human vertebrae during use, wherein the slot opens on the surface.

11. The system of claim 8, wherein the coupling member comprises a hole, wherein the shaft comprises a connector, wherein the connector is configured to pivotably couple with the hole.

12. The system of claim 8, wherein a distal end of the shaft comprises a tee portion, wherein the coupling member comprises a hole, wherein at least part of the tee portion is configured to pivotably couple with the hole.

13. The system of claim 8, further comprising a slide coupled to the shaft, wherein the slide is configured to selectively couple with the coupling member to inhibit rotation of the coupling member with respect to the shaft.

14. The system of claim 13, further comprising a biasing member coupled to the slide, wherein the biasing member is configured to urge the slide toward the coupling member.

15. The system of claim 13, further comprising a locking member coupled to the slide, wherein the locking member is configurable to lock the coupling member in a selected orientation relative to the shaft.

16. A system for inserting a spinal implant in a patient comprising:

a spinal implant;

a coupling member having an end face with one or more elements configured to engage and insert the spinal implant between vertebrae;

a shaft configured to rotatably couple with the coupling member; and a slide slideably disposed over and coupled to the shaft, the slide being axially moveable between a first position spaced from the coupling member and a second position coupled to the coupling member;

wherein the slide is configured to couple with the coupling member to inhibit rotation of the coupling member with respect to the shaft, wherein the shaft and the coupling member are configured to remain coupled when the slide is in the first position, and wherein the slide comprises one or more capture elements, wherein the coupling member comprises one or more cast elements, the one or more capture elements of the coupling member comprising teeth, and wherein at least one capture element of the slide is configured to selectively couple with at least one capture element of the coupling member to inhibit rotation of the coupling member with respect to the shaft.

17. The system of claim 16, further comprising a biasing member coupled to the slide, wherein the biasing member is configured to urge the slide toward the coupling member.

18. The system of claim 16, further comprising a locking member coupled to the slide, wherein the locking member is configurable to lock the coupling member relative to the shaft.

19. The system of claim 16, wherein the slide comprises indicia.

20. The system of claim 16, wherein the slide is configured to selectively couple with the coupling member to inhibit rotation of the coupling member at selected positions between a first position and a second position.

21. The system of claim 20, wherein the slide is configured to selectively couple with the coupling member to inhibit rotation of the coupling member in at least three positions between the first position and the second position with respect to the shaft.

* * * * *